United States Patent
Andrews et al.

(10) Patent No.: US 8,016,972 B2
(45) Date of Patent: Sep. 13, 2011

(54) METHODS AND APPARATUS FOR APPLICATION OF NESTED ZERO WASTE EAR TO TRAVELING WEB

(75) Inventors: Robert E Andrews, Sheboygan, WI (US); Jeff W Fritz, Plymouth, WI (US); Noel Horneck, Glenbeulah, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 387 days.

(21) Appl. No.: 12/151,667

(22) Filed: May 8, 2008

(65) Prior Publication Data

US 2008/0276439 A1    Nov. 13, 2008

Related U.S. Application Data

(60) Provisional application No. 60/928,305, filed on May 9, 2007.

(51) Int. Cl.
*B32B 38/04* (2006.01)
*B32B 38/18* (2006.01)

(52) U.S. Cl. ........ 156/265; 156/250; 156/252; 156/256; 156/259; 156/263; 156/264

(58) Field of Classification Search .......... 156/250, 156/252, 256, 259, 263–265
See application file for complete search history.

(56) References Cited

U.S. PATENT DOCUMENTS

| | | | |
|---|---|---|---|
| 135,145 A | 1/1873 | Murphy | |
| 293,353 A | 2/1884 | Purvis | |
| 312,257 A | 2/1885 | Cotton et al. | |
| 410,123 A | 8/1889 | Stilwell | |
| 432,742 A | 7/1890 | Stanley | |
| 643,821 A | 2/1900 | Howlett | |
| 1,393,524 A | 10/1921 | Grupe | |
| 1,431,315 A | 10/1922 | Le Moine | |
| 1,605,842 A | 2/1926 | Jones | |

(Continued)

FOREIGN PATENT DOCUMENTS

BE    1007854    11/1995

(Continued)

OTHER PUBLICATIONS

Reciprocating Mechanism, Ingenious Mechanisms for Designers and Inventors, Franklin Jones vol. 1, date unknown, 2 pages.

*Primary Examiner* — Mark A Osele
*Assistant Examiner* — Christopher C Caillouet
(74) *Attorney, Agent, or Firm* — Ryan Kromholz & Manion, S.C.

(57) ABSTRACT

The present invention provides a process wherein a rotary knife or die, with one or more cutting edges, turns against and in coordination with a corresponding cylinder to create preferably trapezoidal ears. Ear material is slit into two lanes, one for a left side of a diaper and the other for a right side of a diaper. Fastening tapes are applied to both the right and the left ear webs. The ear material is then die cut with a nested pattern on a synchronized vacuum anvil. The resulting discrete ear pieces however, due to the trapezoidal pattern of the ears, alternate between a correct orientation and an incorrect (reversed) orientation. The reversed ear is required to be rotated 180° into the correct orientation such that the ears and associated tape present a left ear and a right ear on the diaper.

4 Claims, 10 Drawing Sheets

U.S. PATENT DOCUMENTS

| | | |
|---|---|---|
| 1,686,595 A | 10/1928 | Belluche |
| 1,957,651 A | 5/1934 | Joa |
| 2,009,857 A | 7/1935 | Potdevin |
| 2,054,832 A | 9/1936 | Potdevin |
| 2,117,432 A | 5/1938 | Linscott |
| 2,128,746 A | 8/1938 | Joa |
| 2,131,808 A | 10/1938 | Joa |
| 2,171,741 A | 5/1939 | Cohn et al. |
| 2,164,408 A | 7/1939 | Joa |
| 2,167,179 A | 7/1939 | Joa |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,627,859 A | 2/1953 | Hargrave |
| 2,695,025 A | 11/1954 | Andrews |
| 2,702,406 A | 2/1955 | Reed |
| 2,721,554 A | 10/1955 | Joa |
| 2,730,144 A | 1/1956 | Joa |
| 2,722,611 A | 12/1956 | Heywood |
| 2,780,253 A | 2/1957 | Joa |
| 2,785,609 A | 3/1957 | Billeb |
| 2,788,786 A | 4/1957 | Dexter |
| 2,811,905 A | 11/1957 | Kennedy, Jr. |
| 2,828,745 A | 4/1958 | Deutz |
| 2,839,059 A | 6/1958 | Joa |
| 2,842,169 A | 7/1958 | Joa |
| 2,851,934 A | 9/1958 | Heywood |
| 2,875,714 A | 3/1959 | Joa |
| 2,890,700 A | 6/1959 | Lonberg-Holm |
| 2,913,862 A | 11/1959 | Sabee |
| 2,939,461 A | 6/1960 | Joa |
| 2,939,646 A | 6/1960 | Stone |
| 2,960,143 A | 11/1960 | Joa |
| 2,990,081 A | 6/1961 | Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,089,494 A | 5/1963 | Schwartz |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,454,442 A | 7/1969 | Heller, Jr. |
| 3,463,413 A | 8/1969 | Smith |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besyno et al. |
| 3,575,170 A | 4/1971 | Clark |
| 3,607,578 A | 9/1971 | Berg et al. |
| 3,618,608 A | 11/1971 | Brink |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,751,224 A | 8/1973 | Wackerle |
| 3,758,102 A | 9/1973 | Munn et al. |
| 3,772,120 A | 11/1973 | Radzins |
| 3,776,798 A | 12/1973 | Milano |
| 3,796,360 A | 3/1974 | Alexeff |
| 3,811,987 A | 5/1974 | Wilkinson et al. |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,901,238 A | 8/1975 | Gellert et al. |
| 3,903,768 A | 9/1975 | Amberg |
| 3,904,147 A | 9/1975 | Taitel et al. |
| 3,918,698 A | 11/1975 | Coast |
| 3,960,646 A | 6/1976 | Wiedamann |
| 3,991,994 A | 11/1976 | Farish |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A | 6/1984 | Achelpohl |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,543,152 A | 9/1985 | Nozaka |
| 4,551,191 A | 11/1985 | Kock et al. |

| | | | | | | |
|---|---|---|---|---|---|---|
| 4,586,199 A | 5/1986 | Birring | 5,252,170 A | 10/1993 | Schaupp | |
| 4,589,945 A | 5/1986 | Polit | 5,267,933 A | 12/1993 | Precoma | |
| 4,603,800 A | 8/1986 | Focke et al. | 5,273,228 A | 12/1993 | Yoshida et al. | |
| 4,610,682 A | 9/1986 | Kopp | 5,308,345 A | 5/1994 | Herrin | |
| 4,614,076 A | 9/1986 | Rathmacher | 5,328,438 A | 7/1994 | Crowley | |
| 4,619,357 A | 10/1986 | Radzins et al. | 5,340,424 A | 8/1994 | Matsushita | |
| 4,634,482 A | 1/1987 | Lammers | 5,368,893 A | 11/1994 | Sommer et al. | |
| 4,641,381 A | 2/1987 | Heran et al. | 5,407,513 A | 4/1995 | Hayden et al. | |
| 4,642,150 A | 2/1987 | Stemmler | 5,415,649 A | 5/1995 | Watanabe et al. | |
| 4,642,839 A | 2/1987 | Urban | 5,421,924 A | 6/1995 | Ziegelhoffer et al. | |
| 4,650,530 A | 3/1987 | Mahoney et al. | 5,424,025 A | 6/1995 | Hanschen et al. | |
| 4,663,220 A | 5/1987 | Wisneski et al. | 5,429,576 A | 7/1995 | Doderer-Winkler | |
| 4,672,705 A | 6/1987 | Bors et al. | 5,435,802 A | 7/1995 | Kober | |
| 4,675,062 A | 6/1987 | Instance | 5,449,353 A | 9/1995 | Watanabe et al. | |
| 4,693,056 A | 9/1987 | Raszewski | 5,464,401 A | 11/1995 | Hasse et al. | |
| 4,701,239 A | 10/1987 | Craig | 5,486,253 A | 1/1996 | Otruba | |
| 4,723,698 A | 2/1988 | Schoonderbeek | 5,494,622 A | 2/1996 | Heath et al. | |
| 4,726,874 A | 2/1988 | VanVliet | 5,531,850 A | 7/1996 | Hermann | |
| 4,726,876 A | 2/1988 | Tomsovic et al. | 5,540,647 A | 7/1996 | Weiermann et al. | |
| 4,743,241 A | 5/1988 | Igaue et al. | 5,545,275 A | 8/1996 | Herrin et al. | |
| 4,751,997 A | 6/1988 | Hirsch | 5,545,285 A | 8/1996 | Johnson | |
| 4,753,429 A | 6/1988 | Irvine et al. | 5,552,013 A | 9/1996 | Ehlert et al. | |
| 4,756,141 A | 7/1988 | Hirsch et al. | 5,556,360 A | 9/1996 | Kober et al. | |
| 4,764,325 A | 8/1988 | Angstadt | 5,556,504 A | 9/1996 | Rajala et al. | |
| 4,765,780 A | 8/1988 | Angstadt | 5,560,793 A | 10/1996 | Ruscher et al. | |
| 4,776,920 A | 10/1988 | Ryan | 5,602,747 A | 2/1997 | Rajala | |
| 4,777,513 A | 10/1988 | Nelson | 5,624,420 A | 4/1997 | Bridges et al. | |
| 4,782,647 A | 11/1988 | Williams et al. | 5,624,428 A | 4/1997 | Sauer | |
| 4,785,986 A | 11/1988 | Daane et al. | 5,628,738 A | 5/1997 | Suekane | |
| 4,795,510 A | 1/1989 | Wittrock et al. | 5,634,917 A | 6/1997 | Fujioka et al. | |
| 4,798,353 A | 1/1989 | Peugh | 5,643,165 A | 7/1997 | Klekamp | |
| 4,801,345 A | 1/1989 | Dussaud et al. | 5,643,396 A | 7/1997 | Rajala et al. | |
| 4,802,570 A | 2/1989 | Hirsch et al. | 5,645,543 A | 7/1997 | Nomura et al. | |
| 4,840,609 A | 6/1989 | Jones et al. | 5,659,229 A | 8/1997 | Rajala | |
| 4,845,964 A | 7/1989 | Bors et al. | 5,660,657 A | 8/1997 | Rajala et al. | |
| 4,864,802 A | 9/1989 | D'Angelo | 5,660,665 A | 8/1997 | Jalonen | |
| 4,880,102 A | 11/1989 | Indrebo | 5,683,376 A | 11/1997 | Kato et al. | |
| 4,888,231 A | 12/1989 | Angstadt | RE35,687 E | 12/1997 | Igaue et al. | |
| 4,892,536 A | 1/1990 | Des Marais et al. | 5,693,165 A | 12/1997 | Schmitz | |
| 4,904,440 A | 2/1990 | Angstadt | 5,699,653 A | 12/1997 | Hartman et al. | |
| 4,908,175 A | 3/1990 | Angstadt | 5,705,013 A * | 1/1998 | Nease et al. | ................... 156/260 |
| 4,909,019 A | 3/1990 | Delacretaz et al. | 5,707,470 A | 1/1998 | Rajala et al. | |
| 4,925,520 A | 5/1990 | Beaudoin et al. | 5,711,832 A | 1/1998 | Glaug et al. | |
| 4,927,322 A | 5/1990 | Schweizer et al. | 5,725,518 A | 3/1998 | Coates | |
| 4,927,582 A | 5/1990 | Bryson | 5,745,922 A | 5/1998 | Rajala et al. | |
| 4,937,887 A | 7/1990 | Schreiner | 5,746,869 A | 5/1998 | Hayden et al. | |
| 4,963,072 A | 10/1990 | Miley et al. | 5,749,989 A | 5/1998 | Linman et al. | |
| 4,987,940 A | 1/1991 | Straub et al. | 5,788,797 A | 8/1998 | Herrin et al. | |
| 4,994,010 A | 2/1991 | Doderer-Winkler | 5,817,199 A | 10/1998 | Brennecke et al. | |
| 5,000,806 A | 3/1991 | Merkatoris et al. | 5,829,164 A | 11/1998 | Kotitschke | |
| 5,021,111 A | 6/1991 | Swenson | 5,836,931 A | 11/1998 | Toyoda et al. | |
| 5,025,910 A | 6/1991 | Lasure et al. | 5,858,012 A | 1/1999 | Yamaki et al. | |
| 5,045,039 A | 9/1991 | Bay | 5,865,393 A | 2/1999 | Kreft et al. | |
| 5,062,597 A | 11/1991 | Martin et al. | 5,868,727 A | 2/1999 | Barr et al. | |
| 5,064,179 A | 11/1991 | Martin | 5,876,027 A | 3/1999 | Fukui et al. | |
| 5,064,492 A | 11/1991 | Friesch | 5,876,792 A | 3/1999 | Caldwell | |
| 5,080,741 A | 1/1992 | Nomura et al. | 5,879,500 A | 3/1999 | Herrin et al. | |
| 5,094,658 A | 3/1992 | Smithe et al. | 5,902,431 A | 5/1999 | Wilkinson et al. | |
| 5,096,532 A | 3/1992 | Neuwirth et al. | 5,932,039 A | 8/1999 | Popp et al. | |
| 5,108,017 A | 4/1992 | Adamski et al. | 5,938,193 A | 8/1999 | Bluemle et al. | |
| 5,109,767 A | 5/1992 | Nyfeler et al. | 5,964,390 A | 10/1999 | Borresen et al. | |
| 5,110,403 A | 5/1992 | Ehlert | 5,964,970 A | 10/1999 | Woolwine et al. | |
| 5,127,981 A | 7/1992 | Straub et al. | 6,022,443 A * | 2/2000 | Rajala et al. | ................... 156/302 |
| 5,131,525 A | 7/1992 | Musschoot | 6,036,805 A | 3/2000 | McNichols | |
| 5,133,511 A | 7/1992 | Mack et al. | 6,043,836 A | 3/2000 | Kerr et al. | |
| 5,147,487 A | 9/1992 | Nomura et al. | 6,050,517 A | 4/2000 | Dobrescu et al. | |
| 5,163,594 A | 11/1992 | Meyer | 6,074,110 A | 6/2000 | Verlinden et al. | |
| 5,171,239 A | 12/1992 | Igaue et al. | 6,076,442 A | 6/2000 | Arterburn et al. | |
| 5,176,244 A | 1/1993 | Radzins et al. | 6,098,249 A | 8/2000 | Toney et al. | |
| 5,183,252 A | 2/1993 | Wolber et al. | 6,123,792 A | 9/2000 | Samida et al. | |
| 5,188,627 A | 2/1993 | Igaue et al. | 6,171,432 B1 | 1/2001 | Brisebois et al. | |
| 5,190,234 A | 3/1993 | Ezekiel | 6,183,576 B1 | 2/2001 | Couillard et al. | |
| 5,195,684 A | 3/1993 | Radzins | 6,210,386 B1 | 4/2001 | Inoue | |
| 5,203,043 A | 4/1993 | Riedel | 6,212,859 B1 | 4/2001 | Bielik, Jr. et al. | |
| 5,213,645 A | 5/1993 | Nomura et al. | 6,250,048 B1 | 6/2001 | Linkiewicz | |
| 5,222,422 A | 6/1993 | Benner, Jr. et al. | 6,264,784 B1 | 7/2001 | Menard et al. | |
| 5,223,069 A | 6/1993 | Tokuno et al. | 6,276,421 B1 | 8/2001 | Valenti et al. | |
| 5,226,992 A | 7/1993 | Morman | 6,276,587 B1 | 8/2001 | Borresen et al. | |
| 5,246,433 A | 9/1993 | Hasse et al. | 6,306,122 B1 | 10/2001 | Narawa et al. | |

| | | | | | | |
|---|---|---|---|---|---|---|
| 6,309,336 B1 | 10/2001 | Muessig et al. | | 2004/0007328 A1 | 1/2004 | Popp et al. |
| 6,312,420 B1 | 11/2001 | Sasaki et al. | | 2004/0016500 A1 | 1/2004 | Tachibana et al. |
| 6,314,333 B1 | 11/2001 | Rajala et al. | | 2004/0112517 A1 | 6/2004 | Groves et al. |
| 6,315,022 B1 | 11/2001 | Herrin et al. | | 2004/0164482 A1 | 8/2004 | Edinger |
| 6,336,921 B1 | 1/2002 | Kato et al. | | 2004/0182497 A1 | 9/2004 | Lowrey |
| 6,358,350 B1 | 3/2002 | Glaug et al. | | 2005/0000628 A1 | 1/2005 | Norrley |
| 6,369,291 B1 | 4/2002 | Uchimoto et al. | | 2005/0022476 A1 | 2/2005 | Hamer et al. |
| 6,375,769 B1 | 4/2002 | Quereshi et al. | | 2005/0077418 A1 | 4/2005 | Werner et al. |
| 6,391,013 B1 | 5/2002 | Suzuki et al. | | 2005/0139713 A1 | 6/2005 | Weber et al. |
| 6,416,697 B1 | 7/2002 | Venturino et al. | | 2005/0196538 A1 | 9/2005 | Sommer et al. |
| 6,431,038 B2 | 8/2002 | Couturier | | 2005/0230056 A1 | 10/2005 | Meyer et al. |
| 6,443,389 B1 | 9/2002 | Palone | | 2005/0230449 A1 | 10/2005 | Meyer et al. |
| 6,446,795 B1 | 9/2002 | Allen et al. | | 2005/0233881 A1 | 10/2005 | Meyer |
| 6,473,669 B2 | 10/2002 | Rajala et al. | | 2005/0234412 A1 | 10/2005 | Andrews et al. |
| 6,475,325 B1 | 11/2002 | Parrish et al. | | 2005/0257881 A1 | 11/2005 | Coose et al. |
| 6,478,786 B1 | 11/2002 | Gloug et al. | | 2005/0275148 A1 | 12/2005 | Beaudoin et al. |
| 6,482,278 B1 | 11/2002 | McCabe et al. | | 2006/0021300 A1 | 2/2006 | Tada et al. |
| 6,494,244 B2 | 12/2002 | Parrish et al. | | 2006/0137298 A1 | 6/2006 | Oshita et al. |
| 6,521,320 B2 | 2/2003 | McCabe et al. | | 2006/0224137 A1 | 10/2006 | McCabe et al. |
| 6,523,595 B1 | 2/2003 | Milner et al. | | 2006/0265867 A1 | 11/2006 | Schaap |
| 6,524,423 B1 | 2/2003 | Hilt et al. | | 2007/0074953 A1 | 4/2007 | McCabe |
| 6,551,228 B1 | 4/2003 | Richards | | 2008/0161766 A1* | 7/2008 | Sablone et al. .......... 604/385.01 |
| 6,551,430 B1 | 4/2003 | Glaug et al. | | FOREIGN PATENT DOCUMENTS | | |
| 6,554,815 B1 | 4/2003 | Umebayashi | | | | |
| 6,572,520 B2 | 6/2003 | Blumle | | CA | 1146129 | 5/1983 |
| 6,581,517 B1 | 6/2003 | Becker et al. | | CA | 1153345 | 9/1983 |
| 6,596,107 B2 * | 7/2003 | Stopher .......................... 156/66 | | CA | 1190078 | 7/1985 |
| 6,596,108 B2 | 7/2003 | McCabe | | CA | 1210744 | 9/1986 |
| 6,605,172 B1 | 8/2003 | Anderson et al. | | CA | 1212132 | 9/1986 |
| 6,605,173 B2 | 8/2003 | Glaug et al. | | CA | 1236056 | 5/1988 |
| 6,637,583 B1 | 10/2003 | Andersson | | CA | 1249102 | 1/1989 |
| 6,648,122 B1 | 11/2003 | Hirsch et al. | | CA | 1292201 | 11/1991 |
| 6,649,010 B2 | 11/2003 | Parrish et al. | | CA | 1307244 | 9/1992 |
| 6,656,309 B1 | 12/2003 | Parker et al. | | CA | 1308015 | 9/1992 |
| 6,659,150 B1 | 12/2003 | Perkins et al. | | CA | 1310342 | 11/1992 |
| 6,659,991 B2 | 12/2003 | Suckane | | CA | 2023816 | 3/1994 |
| 6,675,552 B2 | 1/2004 | Kunz et al. | | CA | 2404154 | 10/2001 |
| 6,684,925 B2 | 2/2004 | Nagate et al. | | CA | 2541194 | 1/2006 |
| 6,722,494 B2 | 4/2004 | Nakakado | | CA | 2559517 | 5/2007 |
| 6,730,189 B1 * | 5/2004 | Franzmann et al. .......... 156/265 | | DE | 102006047280 | 4/2007 |
| 6,743,324 B2 | 6/2004 | Hargett et al. | | EP | 0044206 | 1/1982 |
| 6,758,109 B2 | 7/2004 | Nakakado | | EP | 0048011 | 3/1982 |
| 6,766,817 B2 | 7/2004 | Dias da Silva | | EP | 0089106 | 9/1983 |
| D497,991 S | 11/2004 | Otsubo et al. | | EP | 0099732 | 2/1984 |
| 6,814,217 B2 * | 11/2004 | Blumenthal et al. ....... 198/459.8 | | EP | 0206208 | 6/1986 |
| 6,820,671 B2 | 11/2004 | Calvert | | EP | 0304140 | 8/1987 |
| 6,837,840 B2 | 1/2005 | Yonekawa et al. | | EP | 0439897 | 2/1990 |
| 6,840,616 B2 | 1/2005 | Summers | | EP | 0455231 | 11/1991 |
| 6,852,186 B1 | 2/2005 | Matsuda et al. | | EP | 510251 | 10/1992 |
| 6,875,202 B2 | 4/2005 | Kumasaka et al. | | EP | 0652175 | 5/1995 |
| 6,893,528 B2 | 5/2005 | Middelstadt et al. | | EP | 0811473 | 12/1997 |
| 6,918,404 B2 | 7/2005 | Dias da Silva | | EP | 0901780 | 3/1999 |
| 6,976,521 B2 | 12/2005 | Mlinar et al. | | EP | 0990588 | 4/2000 |
| 6,978,486 B2 | 12/2005 | Zhou et al. | | EP | 1132325 | 9/2001 |
| 7,017,820 B1 | 3/2006 | Brunner | | EP | 1199057 | 4/2002 |
| 7,066,586 B2 | 6/2006 | da Silva | | EP | 1272347 | 1/2003 |
| 7,077,393 B2 | 7/2006 | Ishida | | EP | 1571249 | 9/2005 |
| 7,172,666 B2 | 2/2007 | Groves et al. | | EP | 1619008 | 1/2006 |
| 7,195,684 B2 | 3/2007 | Satoh | | EP | 1707168 | 4/2006 |
| 7,201,345 B2 | 4/2007 | Werner et al. | | EP | 1726414 | 11/2006 |
| 7,214,174 B2 | 5/2007 | Allen et al. | | EP | 1941853 | 9/2008 |
| 7,247,219 B2 | 7/2007 | O'Dowd | | ES | 509706 | 11/1982 |
| 7,587,966 B2 | 9/2009 | Nakakado et al. | | ES | 520559 | 12/1983 |
| 2001/0012813 A1 | 8/2001 | Bluemle | | ES | 296211 | 12/1987 |
| 2001/0017181 A1 | 8/2001 | Otruba et al. | | FR | 2177355 | 11/1973 |
| 2002/0046802 A1 | 4/2002 | Tachibana et al. | | FR | 2252961 | 7/1975 |
| 2002/0059013 A1 | 5/2002 | Rajala et al. | | FR | 0206208 | 12/1986 |
| 2002/0096241 A1 | 7/2002 | Instance | | FR | 2891811 | 4/2007 |
| 2002/0125105 A1 | 9/2002 | Nakakado | | GB | 191101501 | 1/1912 |
| 2003/0000620 A1 | 1/2003 | Herrin et al. | | GB | 439897 | 12/1935 |
| 2003/0015209 A1 | 1/2003 | Gingrass et al. | | GB | 856389 | 12/1960 |
| 2003/0051802 A1 | 3/2003 | Hargett | | GB | 941073 | 11/1963 |
| 2003/0052148 A1 | 3/2003 | Rajala et al. | | GB | 1096373 | 12/1967 |
| 2003/0066585 A1 | 4/2003 | McCabe | | GB | 1126539 | 9/1968 |
| 2003/0083638 A1 | 5/2003 | Malee | | GB | 1346329 | 2/1974 |
| 2003/0084984 A1 | 5/2003 | Glaug | | GB | 1412812 | 11/1975 |
| 2003/0089447 A1 | 5/2003 | Molee et al. | | GB | 2045298 | 10/1980 |
| 2003/0121614 A1 | 7/2003 | Tabor et al. | | GB | 2115775 | 9/1983 |
| 2003/0135189 A1 | 7/2003 | Umebayashi | | GB | 2288316 | 10/1995 |

| | | | | | | |
|---|---|---|---|---|---|---|
| JP | 428364 | 1/1992 | | WO | WO9821134 | 5/1998 |
| JP | 542180 | 2/1993 | | WO | WO 9907319 | 2/1999 |
| JP | 576566 | 3/1993 | | WO | WO 9913813 | 3/1999 |
| JP | 626160 | 2/1994 | | WO | WO9932385 | 7/1999 |
| JP | 626161 | 2/1994 | | WO | WO 9965437 | 12/1999 |
| JP | 6197925 | 7/1994 | | WO | WO 0143682 | 6/2001 |
| JP | 10035621 | 2/1998 | | WO | WO 0172237 | 10/2001 |
| JP | 10-277091 | 10/1998 | | WO | WO0172237 | 10/2001 |
| SE | 0602047 | 5/2007 | | WO | WO2004007329 | 1/2004 |
| WO | WO9403301 | 2/1994 | | WO | WO 2005075163 | 1/2005 |
| WO | WO9747265 | 12/1997 | | | | |
| WO | WO 9747810 | 12/1997 | | | | |

* cited by examiner

METHODS AND APPARATUS FOR APPLICATION OF NESTED ZERO WASTE EAR TO TRAVELING WEB

RELATED APPLICATION

This application claims the benefit of provisional patent application Ser. No. 60/928,305 filed 9 May 2007.

BACKGROUND OF THE INVENTION

The present invention relates to disposable hygiene products and more specifically, to methods and apparatuses for processing disposable hygiene products. More specifically, the invention relates to cutting and applying segments of one web to attach to a disposable diaper.

The invention disclosed herein also relates to apparatus and methods for waste reduction. Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in assembly line fashion. As in many manufacturing operations, waste minimization is a goal in web processing applications, as products having spliced raw materials cannot be sold to consumers. Indeed, due to the rate at which web processing machines run, even minimal waste can cause inefficiencies of scale.

In present systems, waste materials are recycled. However, the act of harvesting recyclable materials from defective product is intensive. That is, recyclable materials are harvested only after an identification of a reject product at or near the end of a process. The result is that recyclable materials are comingled, and harvesting requires the extra step of separating waste components. Therefore, it is beneficial to use up all of incoming rolls, so that a portion of the incoming rolls do not become waste. That objective is accomplished with the present invention When manufacturing hygiene products, such as baby diapers, adult diapers, disposable undergarments, incontinence devices, sanitary napkins and the like, a common method of applying discrete pieces of one web to another is by use of a slip-and-cut applicator. A slip-and-cut applicator is typically comprised of a cylindrical rotating vacuum anvil, a rotating knife roll, and a transfer device. In typical applications, an incoming web is fed at a relatively low speed along the vacuum face of the rotating anvil, which is moving at a relatively higher surface speed and upon which the incoming web is allowed to "slip". A knife-edge, mounted on the rotating knife roll, cuts a off a segment of the incoming web against the anvil face. This knife-edge is preferably moving at a surface velocity similar to that of the anvil's surface. Once cut, the web segment is held by vacuum drawn through holes on the anvil's face as it is carried at the anvil's speed downstream to the transfer point where the web segment is transferred to the traveling web.

Continual improvements and competitive pressures have incrementally increased the operational speeds of disposable diaper converters. As speeds increased, the mechanical integrity and operational capabilities of the applicators had to be improved accordingly.

SUMMARY OF THE INVENTION

The present invention allows for square, and non-square, and preferably trapezoidal, ear webs to be applied to a traveling web, with zero or minimized waste present in the incoming ear web. Zero material is wasted due to the geometry of the chosen ear pattern and its downstream processing.

An ear is a component of a diaper that is grasped and pulled around the waist of a wearer. Typically, ears are secured to the diaper at a first end, and a second free end is typically equipped with securing means, such as a pressure sensitive adhesive, or hook and loop material. As a user grasps an ear and pulls the ear, elasticity provided about the waist region of the diaper allows the free end to be snugly pulled about the waist of a wearer, and coupled to the diaper. Ears can be rectangular or made of irregular shapes.

The present invention provides a process wherein a rotary knife or die, with one or more cutting edges, turns against and in coordination with a corresponding cylinder to create preferably trapezoidal ears. Ear material is slit into two lanes, one for a left side of a diaper and the other for a right side of a diaper. Fastening tapes are applied to both the right and the left ear webs. The ear material is then die cut with a nested pattern on a synchronized vacuum anvil.

The resulting discrete ear pieces however, due to the trapezoidal pattern of the ears, alternate between a correct orientation and an incorrect (reversed) orientation. The reversed ear is required to be rotated 180° into the correct orientation such that the ears and associated tape present a left ear and a right ear on the diaper.

To accomplish the reversal of the ear pattern, discrete ear pieces are picked up at the nested ear pitch by an ear turner assembly that will expand to a pitch large enough for ears to be unnested and allow clearance for every other ear to be rotated. The rotated ears are then unnested and into the correct orientation.

Two ear turner assemblies can be provided, to rotate every other ear applied to the right side of the product, and every other ear applied to the left side of the product. In this manner, for a single product, one of the two ears will have been rotated 180°.

Ear application to a chassis web can be by a bump method (described later) with intermittent adhesive applied to the chassis web, or can be by vacuum transfer.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
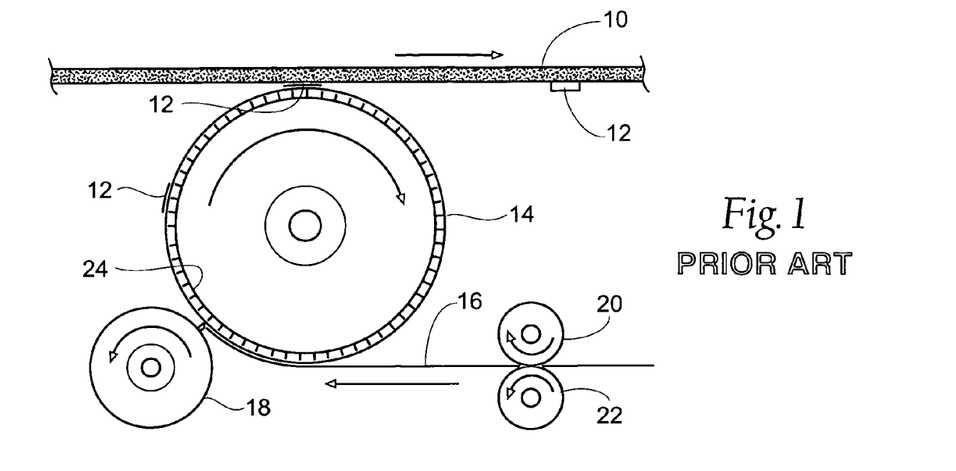
FIG. 1 is a diagrammatic side view of a Prior Art process.
Figure 2:
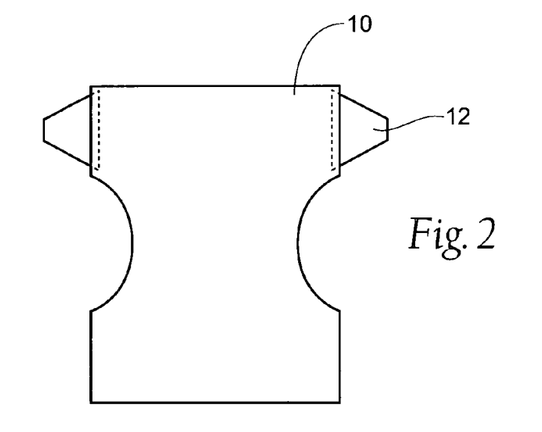
FIG. 2 is a top view of a disposable diaper product carrying a pair of ears.

Referring to the drawings there is seen in FIG. 1 a diagrammatic illustration of a prior art process for applying tabs to webs in a diaper making process, to result in an intermediate product shown in FIG. 2. The present invention can use this prior art method of affixing the segments 12 to the web 10, with a different anvil, the new anvil 114 described below. Web 10 is a composite material used in formation of diapers which is generally formed of various layers of material such as plastic back sheets, absorbent pads and nonwoven topsheets. A series of ears 12 are applied to web 10. In the illustrated process of FIG. 1, a rotatable vacuum anvil 14 is used to supply the ears 12 to web 10. Anvil 14 has internally reduced air pressure or vacuum (not shown), and a plurality of openings 24 are provided through its surface to enable suction of the tab segments 12 against the anvil surface 14. A web of the ear tab forming material 16 is fed by rollers 20 and 22 against the anvil surface 14 where it is cut into segments by a rotary knife 18.

The surface of the anvil roll 14 can have vacuum holes 24 on its smooth surface. In a typical configuration of a slip-and-cut applicator, there is a pattern of vacuum holes 24 distributed to evenly draw the entering web onto the surface of anvil 14 and thence into the cut point where the knife edge 18 engages the anvil 14.

It can be seen from FIG. 1 that in the prior art, the infeed of the ear tab forming material 16 can be at a first speed (with individual ears 12 spaced together), after which the individual ears gain speed to the speed of the anvil 14. Typical infeed speeds could be 120 mm/product for the infeed, while anvil speeds could be 450 mm/product on the anvil. This transition from the slower first speed to the quicker second speed takes place at the cut point, the ear tab forming material 16 slipping on the anvil 14 until cut. However, immediately at the transition cut point 18 from the slower speed to the faster speed, it is desired to place vacuum on the ears because centrifugal force would try to throw the ears off of the vacuum anvil 14.

Ear webs 16 can be comprised of two portions, 12a and 12b, as shown in FIG. 2. Segment 12a is more specifically referred to as the tab section of the ear 12, segment 12b is the ribbon section of the ear 12.

Figure 3:
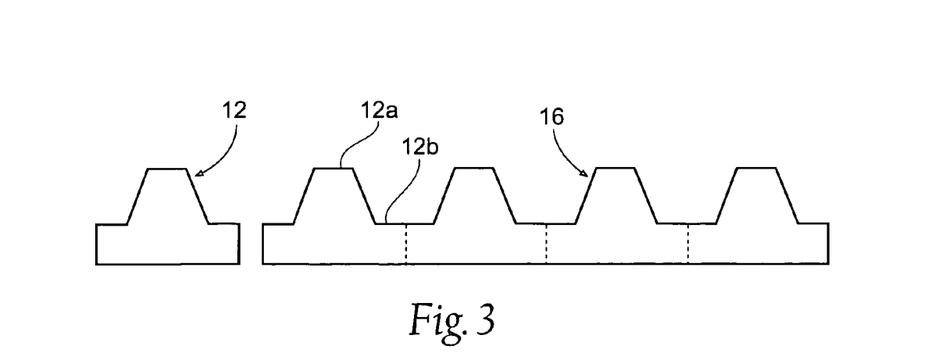
FIG. 3 is a top view of an ear forming web including an individual ear detached from the web.
Figure 6:
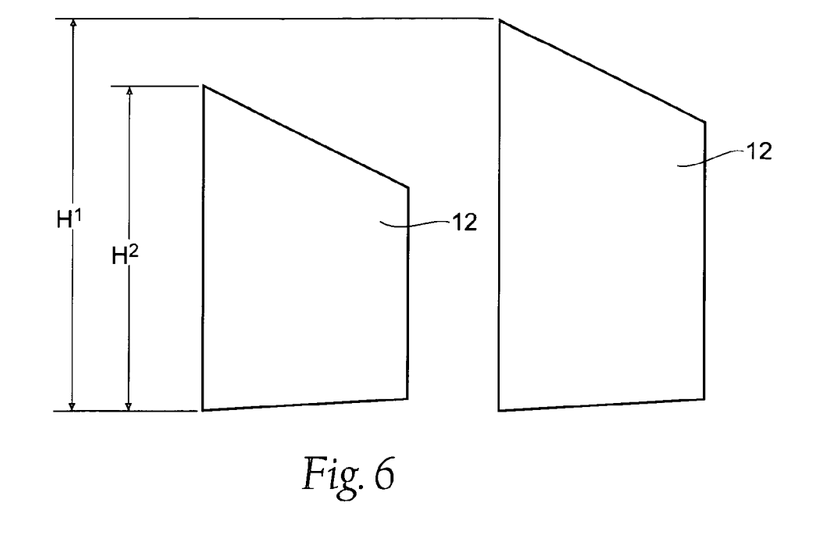
FIG. 6 shows an alternate ear pattern and alternate ear sizes.
Figure 7A:
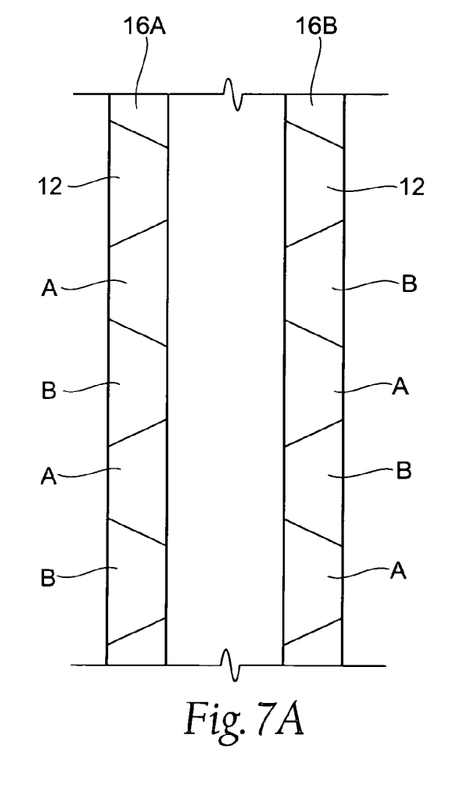
FIGS. 7A, 7B, 7C, 7D, 7E, and 7F are top views of ear webs, FIG. 7A showing non-rotated alternating die cut ear webs, and FIG. 7B showing alternating rotated die cut ear webs, and FIGS. 7C, 7D, 7E, and 7F showing alternate ear configurations.
Figure 7B:
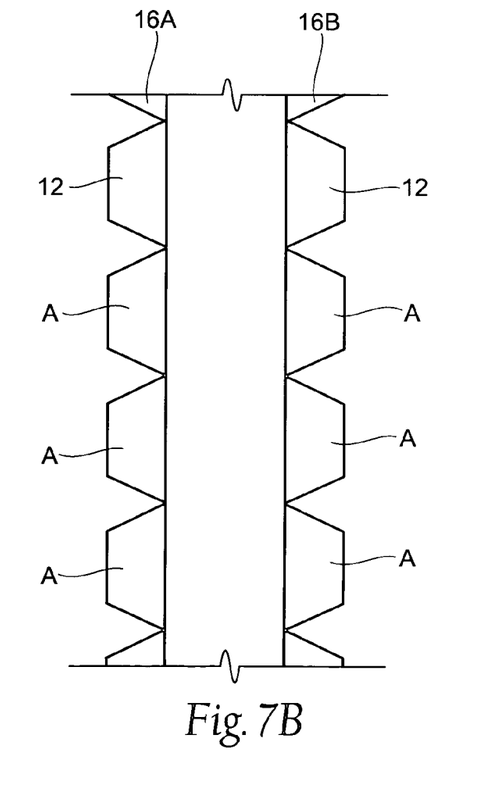

Alternatively, the ears can comprise a trapezoidal shape, as shown in FIGS. 6, 7A and 7B, which will be described later. The trapezoidal shape of FIGS. 7A and 7B is particularly advantageous for zero waste applications, where it is desired to reduce or eliminate the scrapping of raw material. In another zero waste technique, two parallel series of alternating ear webs 16 with ribbon sections of the ear 12 could be created by mirroring the web 16 as shown in FIG. 3 and placing the mirrored web down one/half of an ear length (not shown).

Figure 4:
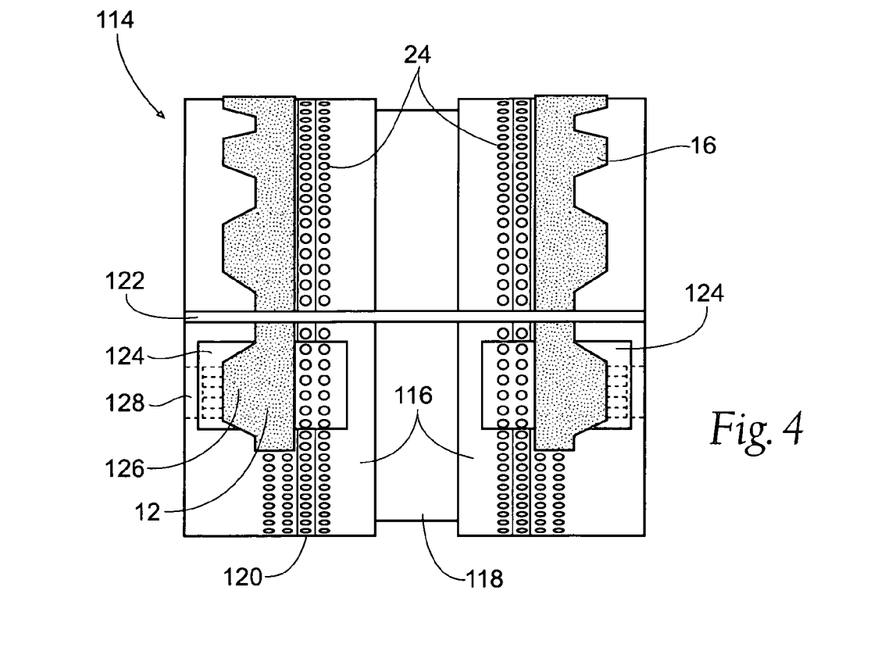
FIG. 4 is a front view of an anvil roll carrying two ear webs.

Referring now to FIG. 4, a front view of an anvil roll 114 is shown carrying ear forming material 16 (and later, an ear 12) in phantom. The anvil roll 114 is preferably formed with two vacuum portions 116 separated by a center groove portion 118. The vacuum portions 116 are preferably mirror images of each other. The anvil roll 114 is symmetrical about a center plane through its circumference. Each vacuum portion 116 contains several circumferential rows of circular vacuum holes 24. Each vacuum portion 116 may also contain a circumferential groove 120 with an additional circumferential row of vacuum holes 24 located in the circumferential groove 120.

Still referring to FIG. 4, two diametrically opposed anvil pockets 122 and two diametrically opposed pairs of ear retaining portions 124 are shown. The ear retaining portions can be created as inserts, with different vacuum patterns applied as the user deems necessary. Each anvil pocket 122 is a groove which extends across the face of the entire anvil roll 114. One ear retaining portion 124 is located on each of the vacuum portions 116. Each ear retaining portion 124 has an ear vacuum hole pattern 126 made of a plurality of vacuum holes 24 located at or near the surface of the anvil roll 144. A plurality of rows of vacuum holes 24 can be employed, each row having a plurality of vacuum holes 24, although more or less than those configurations or patterns shown can be used.

Figure 5:
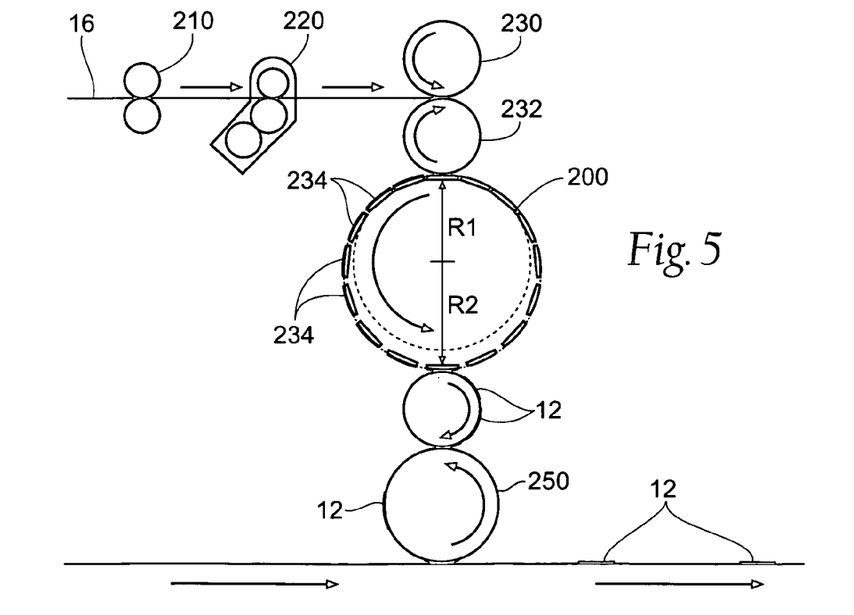
FIG. 5 is a schematic view of a nested zero waste back ear applicator device and methods of the present invention.

Referring now to FIG. 5, a schematic view of a nested zero waste ear applicator device and methods of the present invention are shown. Components of this ear applicator include a web slitter 210, which processes incoming ear web material 16 into two parallel paths (not shown from this view). After being slit, ear web material is processed by tape applicator 220, which can add tape to the ears for securing the ears 12 about the waist of a wearer.

After slitting and application of the tape to the ear web 16, an ear die is used to cut the ear web 16 into the pattern shown in FIG. 7A. The ear material 16 is die cut with a nested pattern on a synchronized vacuum anvil/die combination 230/232.

Referring still to FIG. 5, the cutting edges of the ear dies 230 turn against and in coordination with a corresponding anvil 232 to create preferably trapezoidal ears. It is noted that as shown in FIG. 6, ears 12 having different heights, H1 and H2, can be produced in this configuration by speeding up or slowing down the infeed rate of material 16 into the anvil/die combination 230/232. In this manner, more or less slip is allowed on material 16 prior to cutting, resulting in longer or shorter ears.

Because the ear material 16 has already been slit into two lanes, one for a left side of a diaper and the other for a right side of a diaper, it is noted that two parallel ear dies 230 are used to produce the pattern shown in FIG. 7A to the slit web 16.

The resulting discrete ear pieces however, due to the trapezoidal pattern of the ears shown in FIG. 7A, alternate between a correct orientation A and an incorrect (reversed) orientation B. The reversed ears B are required to be rotated 180° into the correct orientation A such that the ears and associated tape present a left ear and a right ear on the diaper, such as that shown on FIG. 7B. In correct orientation A, such as shown in FIG. 7B, the shorter of the parallel edges of the trapezoid will face toward an outside, left for the left side, and right for the right side. This geometry is desirable to accommodate the legs of the wearer when the ears 12 are pulled about the waist of the wearer.

To accomplish the reversal of the ear pattern, discrete ear pieces are picked up at the nested ear pitch by an ear turner assembly 200 (see FIGS. 5 and 8) that has a series of pucks 234 that travel radially from a minimal radius R1 to a maximal radius R2 at a depositional site. The difference between R1 and R2 is such that individual pucks 235 can be unnested and allow clearance for every other ear to be rotated, as will be described later in relation to FIGS. 10a and 10b. The rotated ears are then unnested and into the correct orientation.

Referring to FIG. 7A, all of the "B" labeled ears 12 on supply 16A will be rotated 180° into an A position. All of the "B" labeled ears 12 on supply 16B will be rotated 180° into an A orientation position.

Figure 7C:
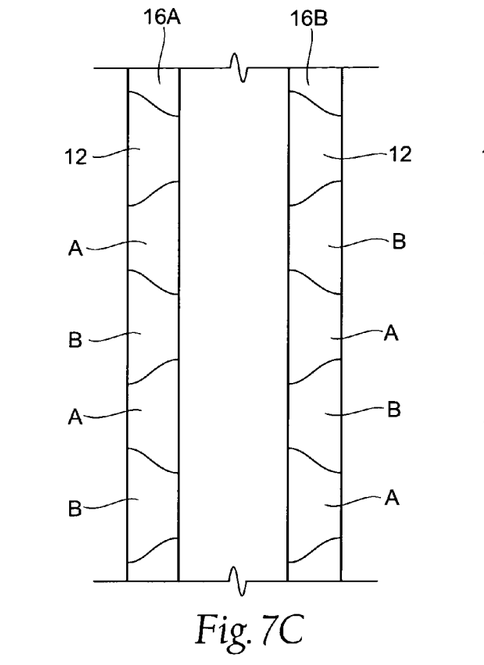
Figure 7D:
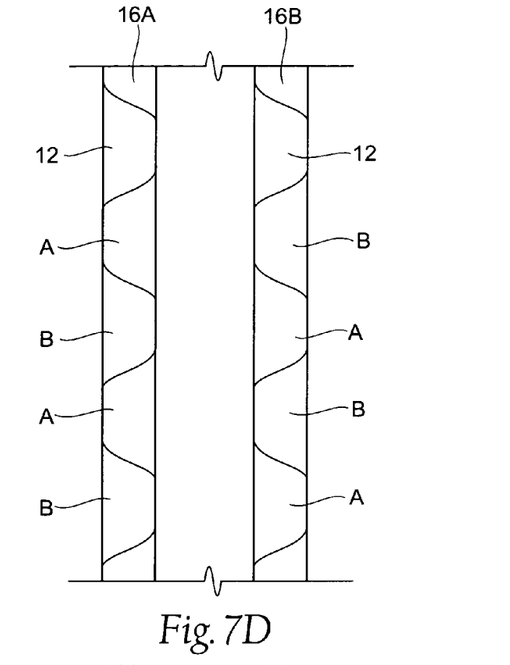
Figure 7E:
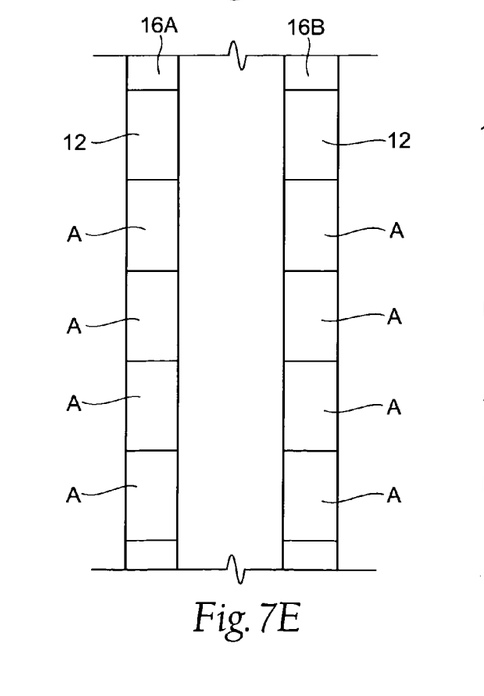
Figure 7F:
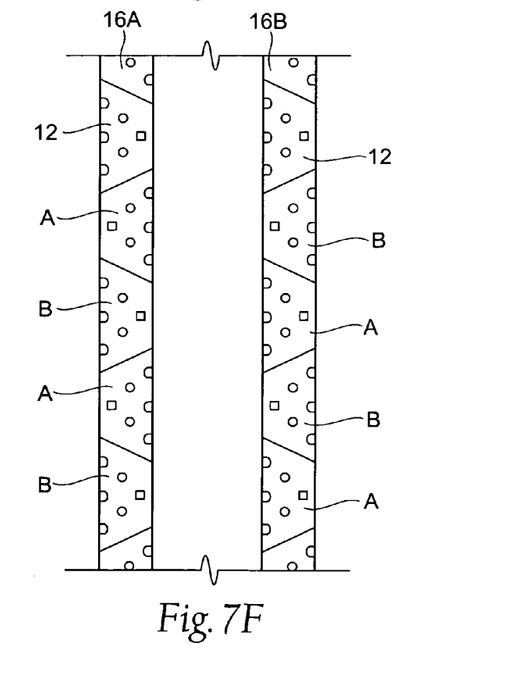

It is noted that ear configurations can vary as shown in FIGS. 7C-7F. In FIGS. 7C and 7D, wavy or curved ear patterns are shown. In FIG. 7E, a square pattern is shown. In FIG. 7F, a trapezoidal pattern is shown. Chips may be cut out in any shape of ear patterns, such as such in FIG. 7F. The chips can be of any shape or size, and can be positioned either on edges of the ears or on the interior of the ears.

Referring now back to FIG. 5, following rotation of every "B" labeled ear 12, each ear is deposited onto vacuum drum 240, rotated and picked up by high vacuum drum 250. Because the ears 12 need to be sped up to match the speed of chassis web 10, the rotation of high vacuum drum 250 is quicker than that of vacuum drum 240. The higher vacuum in drum 250 relative to drum 240 allows the ears 12 to be snatched or grabbed at the higher rotational speed present in drum 250.

Figure 8:
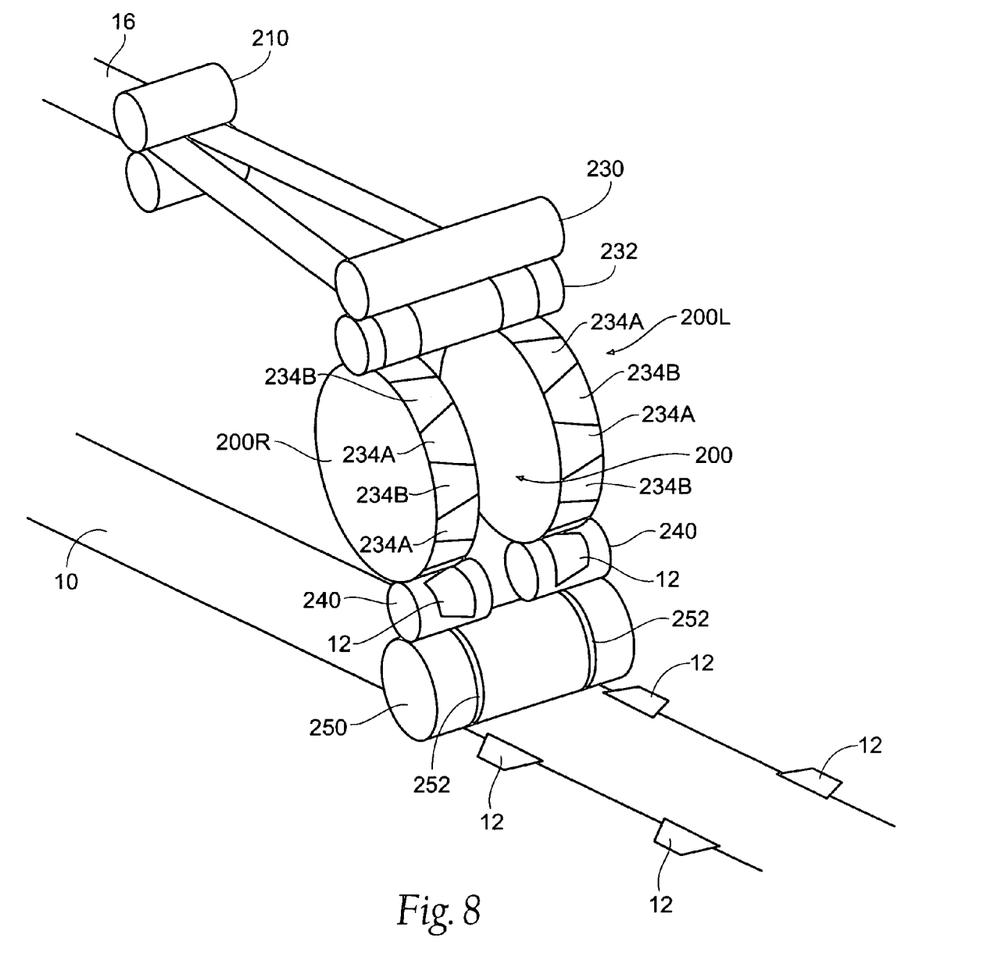
FIG. 8 is a perspective schematic view of the nested zero waste back ear applicator device and methods of the present invention.

Referring now to FIG. 8, a perspective schematic view of the nested zero waste back ear applicator device and methods of the present invention is shown. As can be seen, two ear turner assemblies 200R (right) and 200L (left) are provided, to rotate every other ear 12 applied to the right side of the chassis web 10, and every other ear 12 applied to the left side of the chassis web 10. In this manner, for a single product, one of the two ears will have been rotated 180°.

As can be seen from FIG. 8, two types of pucks are provided, non-rotating pucks 234A and rotating pucks 234B. The non-rotating pucks 234A carry the "A" ears shown in FIG. 7A, or the ones that do not require rotation. The rotating pucks 234B carry the "B" ears shown in FIG. 7A. As the ear turner assemblies 200R and 200L go through their rotation, ears 12 are picked up from the ear die/anvil station 230/232 and rotate about the rotator 200, while every rotating puck 234B also rotates radially during rotation of the rotator 200, as will be described later.

The ears 12 are then deposited onto chassis web 10 and bonded thereto, for instance by ultrasonic bonding ring 252, where the resulting product is sent downstream for further processing.

Figure 9:
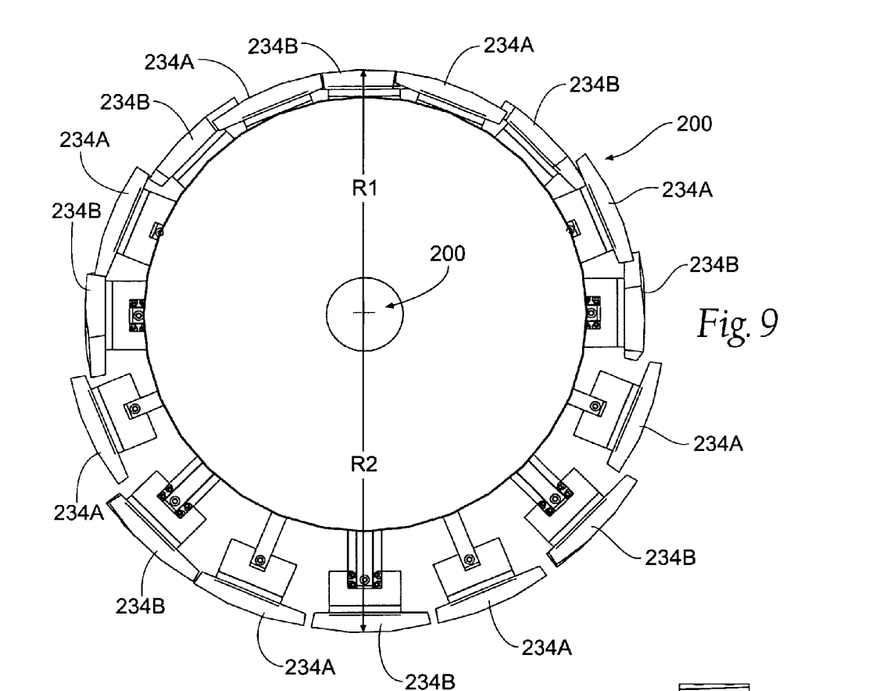
FIG. 9 is a side view of an ear turner assembly device used to rotate alternating ears.
Figure 12:
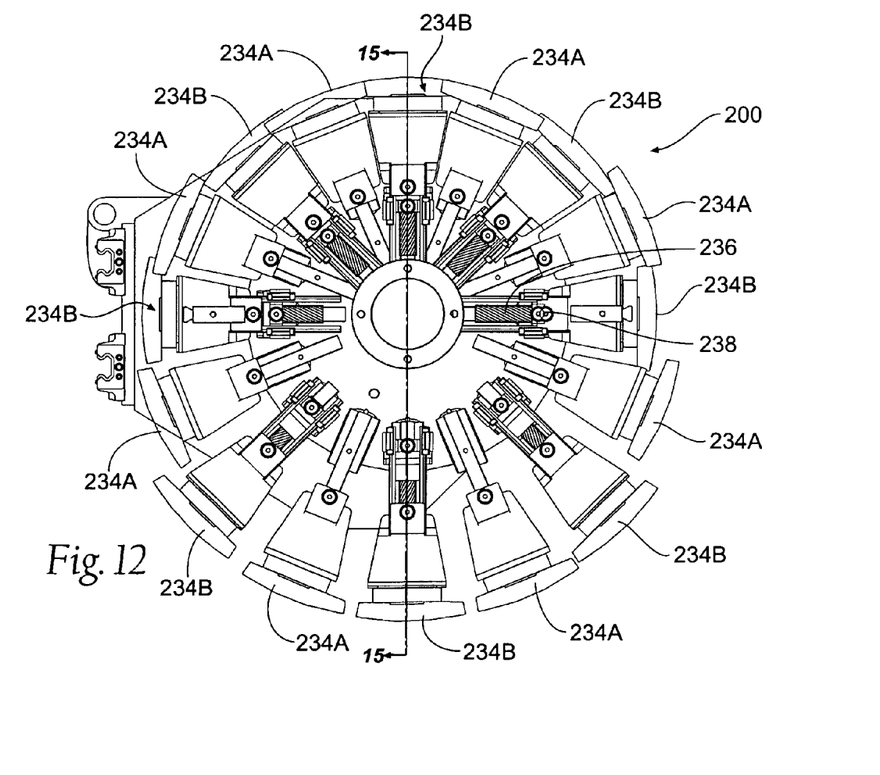
FIG. 12 is a side view of an ear turner assembly device used to rotate alternating ears.

Referring now to FIG. 9 a side view of the ear turner assembly device 200 is shown. The ear turner assembly device 200 used to rotate alternating ears, again with the entire device 200, rotating about a central axis, and each puck 234 traveling radially from a minimal radius R1 to a maximal radius R2 at a depositional site during rotation, and then back to the minimal radius R1. The difference between R1 and R2 is such that individual pucks 235 can be unnested and allow clearance for every other ear to be rotated. Comparing the During rotation from the R1 to the R2 position, rotating pucks 234B undergo not only the increase in radius, but also undergo 180° rotation about an axis perpendicular to the central axis. This can be performed preferably with a screw operation (FIG. 12). During rotation from the R2 position back to the R1 position, the rotating pucks 234B rotate back through their 180° rotation to get to their initial position.

Figure 10A:
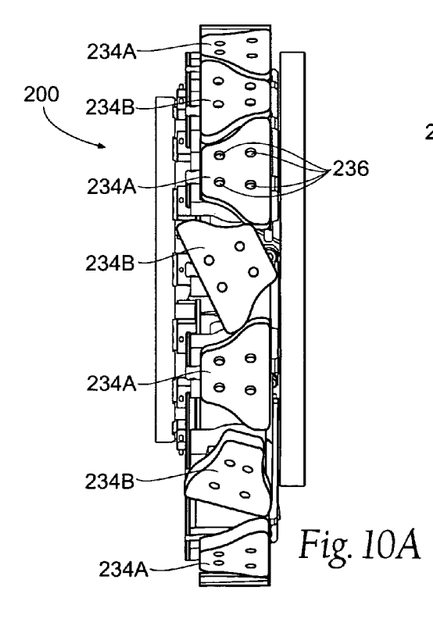
FIG. 10a is front view of the ear turner assembly device used to rotate alternating ears.

Referring now to FIG. 10a, a front view of the ear turner assembly device 200 used to rotate alternating ears is shown. As can be seen, the pucks 234 are each equipped with vacuum voids 236 through which a vacuum is pulled, retaining ears on the rotator device 200 through their rotation until deposition. As can be seen, the pucks 234 are trapezoidal in shape to roughly match the shape of the ears 12. It is also seen from this view that the non-rotating pucks 234A remain in their position relative to the rotating pucks 234B, which rotate from their initial position nested between two non-rotating pucks 234A, and back.

Figure 10B:
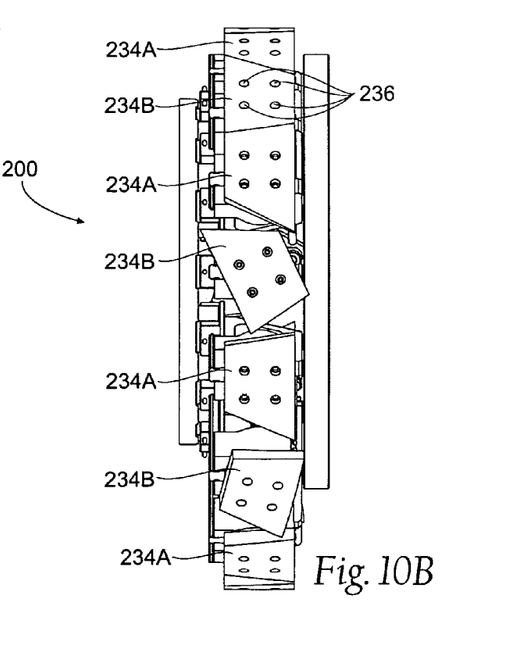
FIG. 10b is front view of the ear turner assembly device used to rotate alternating ears, showing an alternate embodiment of a puck, configured to match in shape and size alternate ear design.

Referring now to FIG. 10B, an alternate shape of the pucks 234 is shown. In FIG. 10A, the pucks 234 are configured to receive wavy shaped ears as described earlier. In FIG. 10B, the pucks 234 are configured to receive trapezoidal shaped ears as described earlier. It is preferable to configure the pucks 234 to match the desired ear pattern.

Figure 11:
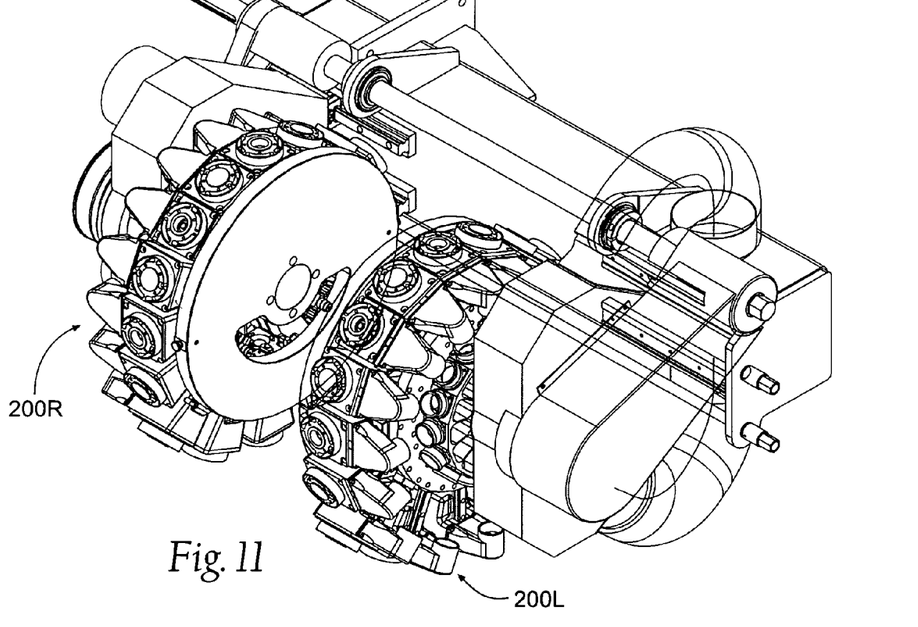
FIG. 11 is a perspective view of two ear turner assembly devices used to rotate alternating ears on a left and a right ear web.
Figure 13:
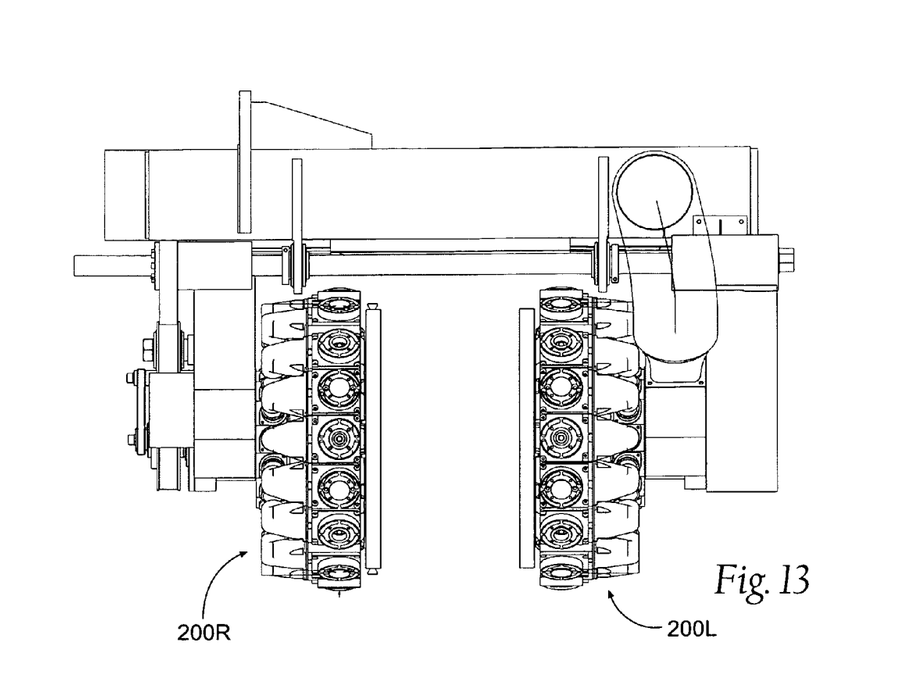
FIG. 13 is a front view two ear turner assembly devices used to rotate alternating ears on a left and a right ear web.
Figure 14:
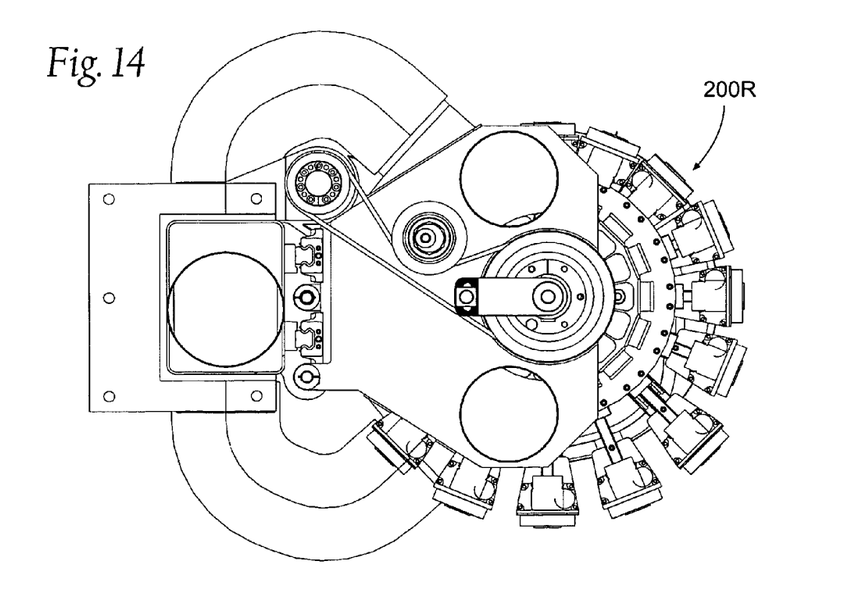
FIG. 14 is a side view of an ear turner assembly device used to rotate alternating ears.

Referring now to FIG. 11, a perspective view of the two ear turner assembly devices 200R and 200L are shown. Also shown are vacuum manifolds used to apply the vacuum to the pucks 234. In this sense, the rotation of the pucks 234 is described in currently pending U.S. application Ser. No. 11/244,387, which is incorporated herein by reference. A front view of this configuration is shown in FIG. 13 and a side view in FIG. 14.

Referring now to FIG. 12 a mechanism for rotating pucks 234b is shown. There, it is seen that screws 236 are provided such that movement of the pucks 234B away from the center axis simultaneously causes rotation of puck 234B. A radially traveling coupling 238 couples the puck with the screw 236, and when the threads of the screw are engaged with the radially traveling coupling 238, rotation is caused.

Figure 15:
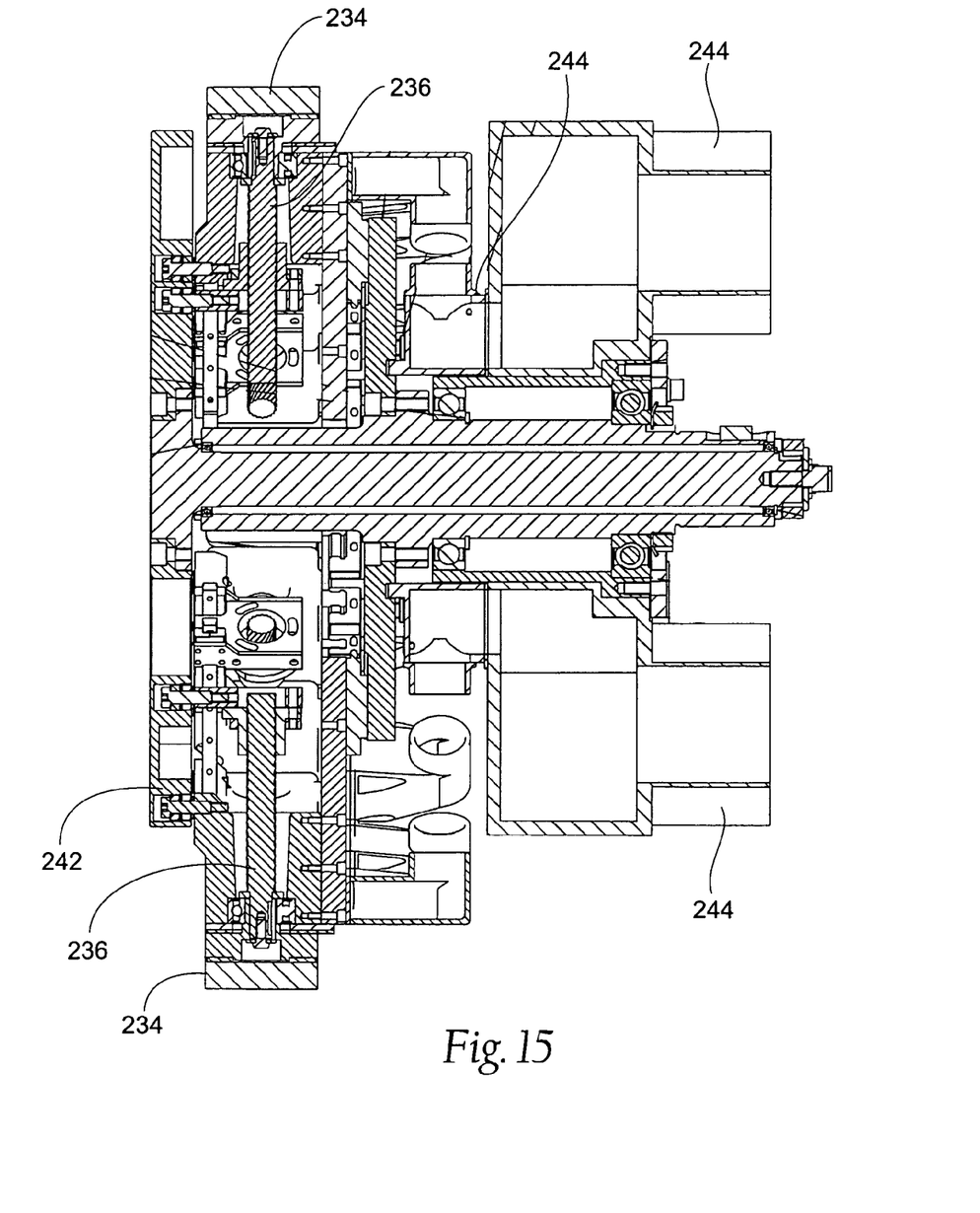
FIG. 15 is a sectional view of the ear turner assembly device used to rotate alternating ears shown in FIG. 10.

FIG. 15 is a cross-sectional view of the ear turner assembly device 200 used to rotate alternating ears along the line shown in FIG. 12. Particularly, screws 236 are operably coupled with pucks or rotator assemblies 234. By rotation of the screw 236, pucks 234 are moved along a radial line in relation to shaft turner 246. Vacuum manifold 244 is provided to commute vacuum to the pucks 234 and ultimately to hold the ears 12 in place. Ear turner cam 242 is provided for rotative purposes.

Figure 16:
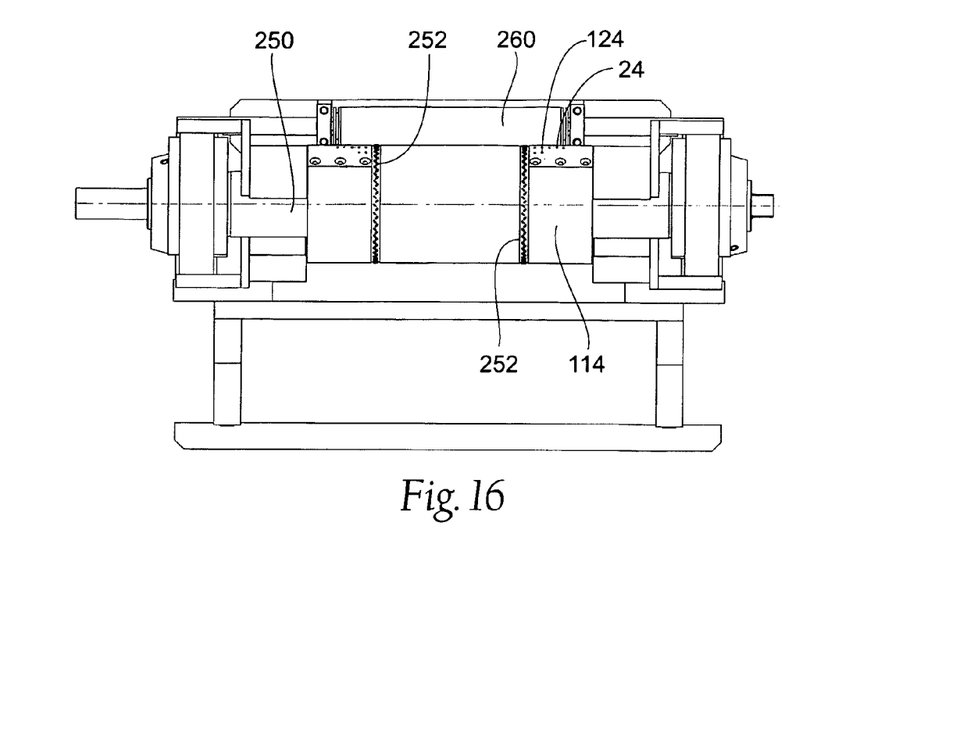
FIG. 16 is a front view of an anvil, ultrasonic bonding ring, and vacuum pattern used for pitch changing ears from a slower web and applying and bonding the ears to a faster moving chassis web.

Referring now to FIG. 16, a front view of a rotatable vacuum wheel 114, ultrasonic bonding ring 252, and vacuum pattern 124 used for pitch changing ears from a slower web and applying and bonding the ears 12 sandwiched between roller 260 and the anvil 114 to a faster moving chassis web is shown.

In this embodiment, the aggressive vacuum pattern 124 on high vacuum drum 250 will have withdrawn ears 12 from vacuum drum 240. This step follows the rotation of the "B" ears as described above. The chassis web 10 is fed in between the roller 260 and the high vacuum drum 250. The ultrasonic bonding ring 252 couples the ears 12 with the chassis web 10 (refer to FIG. 5).

Figure 17:
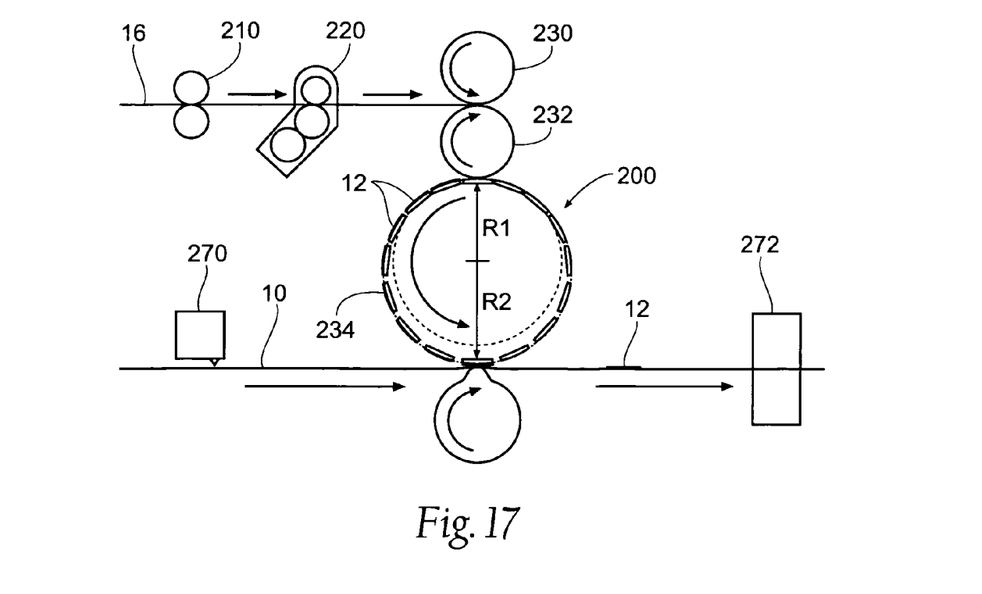
FIG. 17 is a schematic view of the nested zero waste back ear applicator device and methods of the present invention, shown with an alternate embodiment of a means for applying the ear to the chassis web.

Referring now to FIG. 17, a schematic view of the nested zero waste back ear applicator device 200 an alternate embodiment of a means for applying the ear 12 to the chassis web 10 is shown. Instead of the vacuum porting system as previously described, a protuberance carrying rotatable body 274 is urged against the chassis web 10, as disclosed in U.S. Pat. No. 6,475,325, which is incorporated herein as if fully set forth. The disclosure of U.S. Pat. No. 6,475,325 is referred to as the "bump transfer" method. In this embodiment intermittent adhesive is applied to the chassis web 10 at station 270. The intermittent adhesive is applied at intervals to make contact with ears 12 carried by rotating body 200. The protuberance carried by body 274 urges the chassis web 10 towards an ear 12 carried by a puck 234. With the ear 12 coupled with the chassis web, the coupled material is processed by final bonding station 272, after which the ear/chassis combination is sent downstream for further processing as desired.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method of securing an ear to a chassis web, the method comprising:

creating a first left ear from a first infeeding ear web being fed at an infeed speed, the first ear in a left correct facing orientation;

creating a second left ear from the first infeeding ear web, the second ear in a reversed orientation relative to the left correct orientation;

creating a first right ear from a second infeeding ear web being fed at the infeed speed, the first right ear in a reversed orientation relative to a right correct orientation;

creating a second right ear from the second infeeding ear web, the second right ear in the right correct facing orientation;

reorienting the second left ear into the left correct facing orientation;

reorienting the first right ear into the right correct facing orientation;

repitching the ears from the infeed speed at a pickup point to a deposition speed at respective left and right deposition points aligned in the machine direction;

coupling the first left ear and the first right ear onto an infeeding chassis web to create a first chassis and ear assembly at said left and right deposition points aligned in the machine direction at a first position upon the chassis web;

coupling the second left ear and the second right ear onto the infeeding chassis web to create a second chassis and ear assembly at said left and right deposition points aligned in the machine direction at a second position upon the chassis web.

2. The method of claim 1, wherein said first ear is a trapezoidal shape.

3. The method of claim 1, wherein said first ear has at least one curved edge.

4. The method of claim 1, wherein said first and said second ears are symmetrical.

\* \* \* \* \*